United States Patent [19]

Rey et al.

[11] Patent Number: 5,412,092

[45] Date of Patent: May 2, 1995

[54] N-SUBSTITUTED 2-AZETIDINONES

[75] Inventors: Allan W. Rey, Quebec, Canada; Purushotham Vemishetti, E. Syracuse, N.Y.; Roberto Droghini, Quebec, Canada

[73] Assignee: Bristol-Myers Squibb Company, New York, N.Y.

[21] Appl. No.: 165,610

[22] Filed: Dec. 13, 1993

Related U.S. Application Data

[63] Continuation-in-part of Ser. No. 52,434, Apr. 23, 1993, abandoned.

[51] Int. Cl.$^6$ .............. C07D 205/085; C07D 205/08; C07D 405/04; C07D 409/04
[52] U.S. Cl. .............................. 540/200; 540/357; 540/360; 540/364
[58] Field of Search ................ 540/200, 357, 360, 364

[56] References Cited

PUBLICATIONS

Manhas, Synthesis 1981, pp. 209-211.

Primary Examiner—Mark L. Berch
Attorney, Agent, or Firm—Sandra M. Nolan

[57] ABSTRACT

Novel cis compound having the formula:

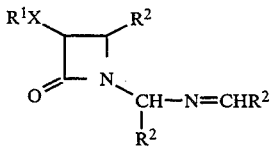

wherein $R^1$ is alkyl, haloalkyl, cycloalkyl, aryl or a carbohydrate derivative; X is O, N, S, C(O)O or a direct bond; and $R^2$ is aryl, substituted aryl or heteroaryl are useful in the synthesis of taxol and taxol derivatives.

8 Claims, No Drawings

N-SUBSTITUTED 2-AZETIDINONES

CROSS-REFERENCE TO RELATED APPLICATION

This application is a continuation-in-part of U.S. Ser. No. 08/052,434, filed Apr. 23, 1993, and now abandoned.

BACKGROUND OF THE INVENTION

The present invention relates to methods for the preparation of N-unsubstituted 2-azetidinones, and to novel compounds useful in said methods.

Taxol, a compound isolated from the bark of Pacific yew trees, has recently emerged as a promising anticancer drug, particularly in the treatment of ovarian cancer. Because taxol is only present in small quantity in the bark of the slow-growing Pacific yew, there is a continuing interest in a practical synthetic or semi-synthetic route to taxol in order to meet the increasing demand for the drug without unduly burdening the Pacific yew population.

U.S. Pat. No. 5,175,315 issued to R. A. Holton on Dec. 29, 1992 discloses the coupling of protected baccatin III with protected N-benzoyl-3-hydroxy-4-phenyl-2-azetidinone (A) to give taxol.

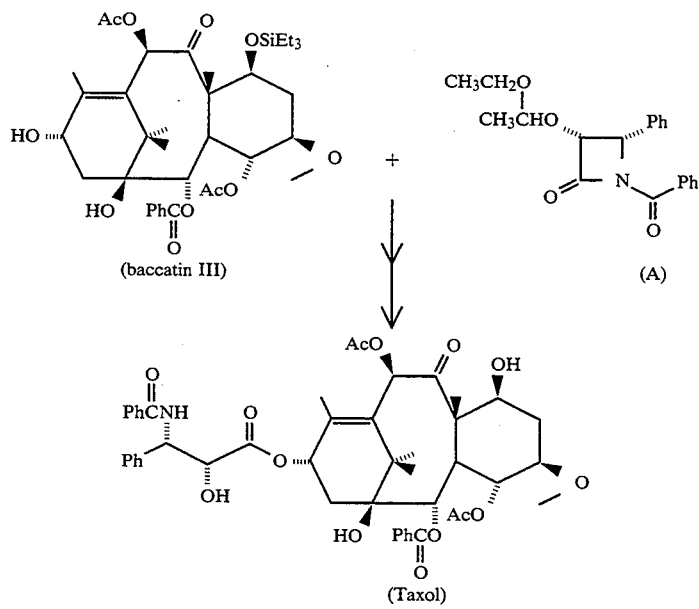

In U.S. Pat. No. 5,175,315 it is disclosed that 3-acetoxy-4-phenyl-2-azetidinone (B), a precursor to (A), is prepared by reacting acetoxyacetyl chloride with N-benzylidene-4-methoxyaniline to give N-(4-methoxyphenyl)-3-acetoxy-4-phenyl-2-azetidinone, followed by removal of the 4-methoxyphenyl group with cerium ammonium nitrate (CAN). This process is also applicable to the synthesis of 2-azetidinones with other 3- and 4-substituents.

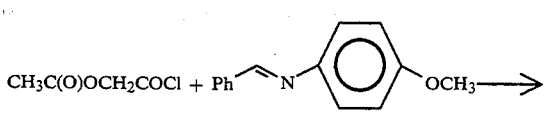

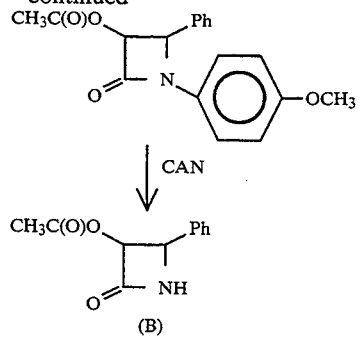

The above process for the preparation of β-lactam (B) requires the use of large quantity of CAN, rendering it impractical as a large scale manufacturing process. Therefore, there is the need for an improved process for the preparation of 3,4-disubstituted-2-azetidinones that is amenable to scale-up production.

Manhas et al, in "Cyanuric Chloride: A Mild Reagent for β-Lactam Synthesis" *Synthesis*, 1981, 209–211, reports the synthesis of 3-azido-4-phenyl-2-azetidinone from potassium azidoacetate, hydrobenzamide and cyanuric acid in the presence of triethylamine, followed by treatment with 10% HCl. Wells and Lee in "The Synthesis of 2-Azetidinones" *J. Org. Chem.*, 1969, 34:1477–1479 reports the synthesis of 3-azido-4-phenyl (and substituted phenyl)-2-azetidinone from azidoacetyl chloride and hydrobenzamide in the presence of triethylamine, followed by treatment with 10% HCl. Neither Manhas nor Wells discloses the isolation of the cycloaddition product; indeed it is reported later (see Synthesis, Sep. 1975, at p. 557) that the cycloadditon product is the dimeric azetidinone (C).

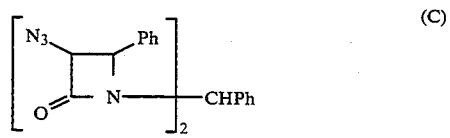

SUMMARY OF THE INVENTION

The present invention provides novel cis-N-iminomethyl-3,4-disubstituted-β-lactams having the formula (I)

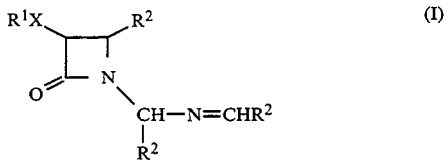

wherein $R^1$ is selected from the group consisting of alkyl, halosubstituted alkyl, aryl, cycloalkyl, arylalkyl and a carbohydrate derivative; X is selected from O, N, S, C(O)O and a direct bond; $R^2$ is selected from the group consisting of aryl, substituted aryl, and heteroaryl.

In another aspect the present invention provides a method for preparing cis-3,4-disubstituted-β-lactams having the formula (I)

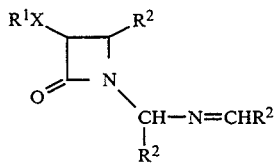

wherein $R^1$, X and $R^2$ are as defined above, which comprises either 1) subjecting a compound of formula (I) to catalytic hydrogenolysis; or 2) treating a compound of formula (I) with an aqueous acid solution in which said acid is selected from the group consisting of sodium bisulfite and acetic acid and formic acid.

In yet another aspect of the invention there is provided a method for preparing a β-lactam of formula (II) which comprises reacting a compound of the formula $R^1X$-$CH_2C(O)$-L, preferably of formula $R^1C(O)OCH_2$-C(O)-L, with a compound of the formula $R^2$-CH-(N=CHR$^2$)$_2$ (L is a leaving group; $R^1$, X and $R^2$ are as defined above) in the presence of a base, and maintaining the reaction temperature at or below about 5° C.; followed by either 1) subjecting the compound thus produced to catalytic hydrogenolysis; or 2) treating the compound thus produced with an aqueous acid solution in which said acid is selected from the group consisting of sodium bisulfite, acetic acid and formic acid.

DETAILED DESCRIPTION OF THE INVENTION

In the application, unless otherwise specified, the following definitions are applicable. "Alkyl" means a saturated straight or branched carbon chain having from one to six carbon atoms; examples of alkyl are methyl, ethyl, n-propyl, isopropyl, n-butyl, sec-butyl, tert-butyl, n-pentyl, neo-pentyl and n-hexyl. "Aryl" means a mono- or bicyclic aromatic carbocyclic group; examples of aryl are phenyl and naphthyl. "Halo-substituted alkyl" means an alkyl group bearing at least one halogen atom selected from fluorine, chlorine, bromine and iodine; examples of halo-substituted alkyl include chloromethyl, bromomethyl, trifluoromethyl, trichloroethyl and iodoethyl. "Cycloalkyl" means a saturated carbocyclic group having three to six carbon atoms; examples of cycloalkyl are cyclopropyl, cyclobutyl, cyclopentyl and cyclohexyl. "Substituted aryl" means an aryl group bearing from one to three same or different substituents selected from $C_{1-3}$ alkyl, $C_{1-3}$ alkoxy, hydroxy, trifluoromethyl, and halogen. "Heteroaryl" means a mono- or bicyclic aromatic group having five to six atoms in each ring, and having at least one ring heteroatom selected from nitrogen, sulfur and oxygen; examples of heteroaryl are furyl and thienyl. "Arylalkyl" means groups conforming to the structure aryl CH(alkyl)-. "Carbohydrate derivative" means groups derived from carbohydrates containing a pyranosyl or furanosyl ring; examples of carbohydrate derivatives include the 4,6-di-O-acetoxy-2,3-dideoxy-α-D-glucopyranosyl moiety and the like. "β-lactam" and "2-azetidinone" are used interchangeably.

Compounds of formula (I) are useful intermediates in the preparation of cis-3-acyloxy-4-substituted-2-azetidinones which in turn can be converted to cis-1-acyl-3-protected hydroxy-4-substituted-2-azetidinones that are then used to acylate baccatin III to produce taxol or derivatives thereof.

cis-N-Iminomethyl-2-azetidinones of formula (I) may be prepared by cycloaddition of a carboxylate (a) with a bis-imine (b) in the presence of a base, as depicted in Scheme I.

SCHEME I $R^1$—X—$CH_2C(O)$—L + $R^2CH$—(N=CHR$^2$)
(a) (b)

↓ Base

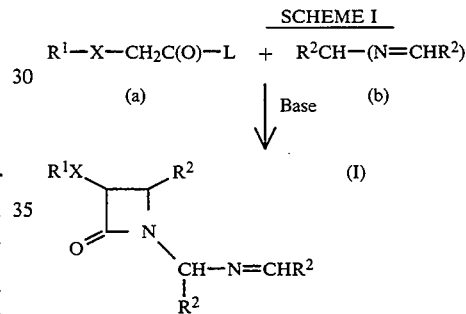

In Scheme I, $R^1$, X and $R^2$ are as defined previously. L is a conventional leaving group such as an acetate, e.g. trifluoroacetate; an alkoxide or an alkylthio group, e.g. methoxide, ethoxide, or methylthio; and halide; preferably L is chloride. In compounds of formula (I) preferred $R^1$ are alkyl, halo-substituted alkyl, aryl, arylalkyl, and carbohydrate derivative groups. More preferred $R^1$ are alkyl, more particularly methyl and isopropyl; chloroalkyl, more particularly chloromethyl; aryl, more particularly phenyl; arylalkyl, particularly phenylethyl; and a carbohydrate derivative, particularly 4,6-di-O-acetoxy-2',3'-dideoxy-α-D-glucopyranosyl. The most preferred $R^1$ is methyl. X is selected from O, N, S, C(O)O, and a direct bond. Preferred X is O and C(O)O. The most preferred X is C(O)O. Preferred $R^2$ are aryl, substituted aryl, furyl and thienyl; more preferred $R^2$ are phenyl, 4-methylphenyl, 4-methoxyphenyl, 2-furyl and 2-thienyl.

The cycloaddition reaction is carried out in an inert organic solvent. The identity of the solvent is not particularly critical so long as it does not interfere with the intended reaction, and is not reactive with the starting materials or with the products formed. Thus, suitable solvents are, for example, hydrocarbons, halogenated hydrocarbons, esters, ethers, nitriles, thioethers and the like. Particular solvents that can be mentioned include benzene, toluene, xylenes, methylene chloride, chloroform, 1,2-dichloroethane, ethyl acetate, n-propyl acetate, isobutyl acetate, n-butyl acetate, tetrahydrofuran, t-butyl methyl ether, acetonitrile. Preferred solvents are methylene chloride and ethyl acetate.

The base utilized in the reaction may be a tertiary organic amine base such as trimethylamine, triethylamine, diisopropylethylamine, pyridine and dimethylaminopyridine; or a stronger metal base such as lithium diisopropylamide, $C_{1-6}$alkyl lithium, lithium bis(trimethylsilyl)amide and phenyllithium. When L is halide, a tertiary amine such as triethylamine and diisopropylethylamine is preferably used in the reaction; and when L is other than a halide, a stronger base such as lithium diisopropylamide is preferably used.

The cycloaddition is prone to the formation of unwanted dimeric 2-azetidinone (c). Surprisingly, it was found that the dimer (c) is not suitable for converting into the N-unsubstituted 2-azetidinone of formula (II).

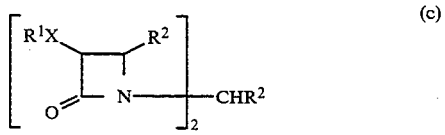
(c)

Thus, in order to maximize the yield of the desired compound of formula (I) the reaction temperature and the relative amounts of the reagents used are controlled. The reaction is conducted at a reduced temperature, preferably the reaction temperature is maintained at or below about 5° C. Most preferably the reaction temperature is maintained at about −20° C. to about 5° C.

In general, for each equivalent of the bis-imine reactant (b) about 0.9 to about 1.5 equivalent of the carboxylate reactant (a), and about 1 to about 1.5 equivalents of the base are used. Typically about 1 to about 1.2 equivalents of reactant (a) and about 1 to about 1.2 equivalents of the base are used per equivalent of reactant (b). The reaction is preferably carried out under inert atmosphere, for example under argon or nitrogen, and is usually complete within 24 hours. The progress of the reaction can be monitored by conventional chromatographic methods such as high pressure liquid chromatography with UV detection.

The cycloaddition product obtained is a mixture of two pairs of diastereomers in which the 3- and 4- substituents on the azetidinone ring are cis to each other. Although the pairs of diastereomers may be separated, it is not necessary to do so. The individual stereoisomers of formula (I) and mixtures thereof are all contemplated to be within the scope of this invention.

The starting materials (a) and (b) are either commercially available or may be readily prepared according to methods well known in the art. Thus, one group of compounds useful as reactant (a) may be prepared by reacting an appropriate acyl chloride, $R^1C(O)Cl$, with glycolic acid to provide acyloxyacetic acid which is in turn derivatized, for example by treatment with thionyl chloride to generate the corresponding acyloxyacetyl chloride.

Another group of useful carboxyl-containing reactants (a) are made by reacting ethyl bromoacetate with the appropriate alkoxide, for instance the alkoxide generated from α-methylbenzyl alcohol. Hydrolysis of the ethyl ester provides the alkyloxyacetic acid which is in turn derivatized by treatment with thionyl chloride to generate the corresponding alkyloxyacetyl chloride.

Other groups of carboxyl-containing reactants (a) are made using a procedure described by Borer and Balogh in "An Asymmetric Synthesis of 3-Hydroxy-β-Lactam by Ketene-Imine Cycloaddition: Utilization of Chirol Ketenes from Carbohydrates", *Tetrahedron Lett.*, 1991, 32: 1039–1040.

The bis-imine reactant (b) is readily prepared from an appropriate aldehyde, $R^2C(O)H$, and concentrated ammonium hydroxide in isopropyl alcohol.

Another aspect of the invention provides the removal of the N-substituent of a β-lactam of formula (I) to give the corresponding N-unsubstituted β-lactam of formula (II) as depicted in Scheme II ($R^1$ and $R^2$ are as previously defined). In one method the N-substituent is removed by catalytic hydrogenolysis; in another method the removal is accomplished with an aqueous acid solution wherein said acid is acetic acid, sodium bisulfite or formic acid.

SCHEME II

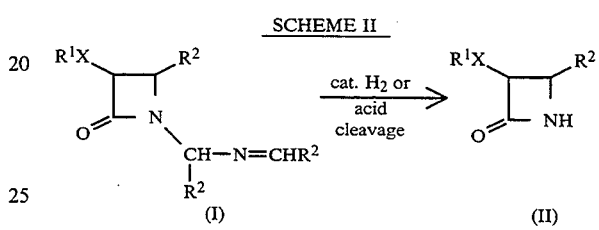

Catalytic hydrogenolysis of a β-lactam of formula (I) is conducted in an inert organic solvent that is not reactive with the reactants, reagents or product formed, and is not reduced under hydrogenation conditions. Examples of suitable solvents include esters such as alkyl acetate, ethers such as t-butyl methyl ether, and alcohol such as ethanol, ketones such as acetone, hydrocarbons such as cyclohexane, or amides such as dimethylformamide.

The catalyst may be one that is conventionally used in hydrogenation, for example, platinum, palladium, nickel, rhodium and ruthenium. Preferably palladium is used. Palladium may be used as palladium on carbon either dry or containing water, or as palladium hydroxide on carbon. Hydrogenation pressure may be from about 2 psi to about 4 atm. Hydrogenation is conducted at a temperature of about 20° to about 30° C.; preferably it is carried out at ambient temperature.

In one preferred embodiment, catalytic hydrogenation is applied to β-lactams of formula (I) wherein $R^1$ is alkyl and X is C(O)O. In another preferred embodiment, catalytic hydrogenation is applied to β-lactams of formula (I) wherein $R^2$ is aryl, substituted aryl or furyl. In yet another preferred embodiment, the catalyst is palladium based. In a more preferred embodiment, catalytic hydrogenation is applied to β-lactams of formula (I) wherein $R^1$ is alkyl; $R^2$ is aryl, substituted aryl or furyl; X is C(O)O; and the catalyst is selected from palladium on carbon and palladium hydroxide on carbon; more preferably, $R^2$ is phenyl, 4-methylphenyl, 4methoxyphenyl or furyl; most preferably $R^1$ is methyl and $R^2$ is phenyl and X is C(O)O.

The N-substituent of a β-lactam of formula (I) may also be cleaved under selected acidic conditions. Thus, in one aspect a β-lactam of formula (I) is treated with aqueous acetic acid. The reaction is carried out in an inert organic solvent such as methylene chloride, ethyl acetate, toluene, and t-butyl methyl ether. Acetic acid is used as 60%–80% (volume in volume), preferably about 70% to about 75%, aqueous solution and can be used in about 2.5 to about 65 equivalents relative to the compound of formula (I); preferably about 5 to about 8 equivalents are used. The reaction is conducted at elevated temperature, for example at reflux of the reaction solution, and is usually complete within about 24 hours.

In another method aqueous sodium bisulfite is used to remove the N-substituent of a compound of formula (I). Sodium bisulfite of commerce, a mixture of sodium bisulfite and sodium metasulfite, can be used directly. Sodium bisulfite, in an amount of about 300 to about 600 g per mole of substrate of formula (I) is used. The reaction is carried out in inert organic solvent at ambient or elevated temperature, for example about 20° to about 60° C.; preferably at about 50° C.

In yet another embodiment, formic acid is employed as a 70 to 98% aqueous solution (w/w), preferably a 90 to 95% solution. Generally the amount of formic acid will provide about 4 to about 10 equivalents relative to formula I. Preferably from about 5 to about 7 equivalents are used. The solvents discussed above are generally useful with formic acid.

In one preferred embodiment, a β-lactam of formula (I) wherein $R^2$ is aryl, substituted aryl or thienyl is converted to the corresponding N-unsubstituted β-lactam of formula (II) with about 70% to about 75% aqueous acetic acid. In another preferred embodiment, the reaction is conducted in an organic solvent selected from halogenated hydrocarbon, alkyl acetate, hydrocarbon, and ether. In a more preferred embodiment, $R^1$ is methyl, $R^2$ is phenyl and X is C(O)O, and the reaction is carried out in methylene chloride using 75% (volume in volume) aqueous acetic acid.

In another preferred embodiment, a β-lactam of formula (I) wherein $R^2$ is aryl or substituted aryl is converted to the corresponding N-unsubstituted β-lactam of formula (II) with aqueous sodium bisulfite. In another preferred embodiment, the reaction is conducted in an organic solvent selected from a halogenated hydrocarbon, an alkyl acetate, a hydrocarbon, and an ether. In a more preferred embodiment, $R^1$ is methyl, $R^2$ is phenyl and X is C(O)O, and the reaction is carried out in methylene chloride or ethyl acetate.

Although the β-lactam of formula (I) can be isolated, it is often advantageous to carry out the cycloaddition reaction and the cleavage of the N-substituent sequentially without isolating the intermediate β-lactam of formula (I). Accordingly, another aspect of the invention provides a process for the preparation of N-unsubstituted β-lactam of formula (II) which comprises contacting a compound of the formula $R^1X$-$CH_2C(O)$-L wherein L is a leaving group, with a compound of the formula $R^2$-CH-(N=$CHR^2$)$_2$ in the presence of a base, and maintaining the reaction temperature at or below about 5° C.; and, without isolating the cycloaddition product, either 1) subjecting the compound thus produced to catalytic hydrogenolysis; or 2) treating the compound thus produced with an aqueous acid solution in which the acid is selected from the group consisting of sodium bisulfite, acetic acid and formic acid; $R^1$, $R^2$, X and L are as previously defined.

In one preferred embodiment, $R^1$ is alkyl, arylalkyl or carbohydrate derivative, $R^2$ is aryl, substituted aryl or furanyl, X is C(O)O or O; and the cycloaddition product is subject to catalytic hydrogenolysis using a palladium-based catalyst. More preferably, the reaction solvent is an alkyl acetate such as ethyl acetate, and the base is triethylamine. In a particularly preferred embodiment, $R^1$ is methyl, $R^2$ is phenyl and X is C(O)O.

In another preferred embodiment, $R^2$ is aryl, substituted aryl or thienyl; and the cycloaddition product is treated with aqueous acetic acid. More preferably, the reaction solvent is a halogenated hydrocarbon such as methylene chloride, the base is diisopropylethylamine, and the acid is 75% aqueous acetic acid. It is particularly preferred that $R^1$ is methyl, $R^2$ is phenyl and X is C(O)O.

The N-unsubstituted β-lactam of formula (II) obtained by the process of the present invention is a racemic mixture of two enantiomers cis-(3R)-3-acyloxy-4-substituted-2-azetidinone (IIa) and cis-(3S)-3-acyloxy-4-substituted-2-azetidinone (IIb).

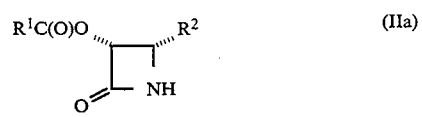

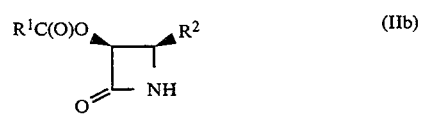

The racemic mixture may be resolved by conventional methods such as conversion to diastereomers, differential absorption on column packed with chiral adsorbents, or enzymatically. For example, the racemic mixture may be contacted with an enzyme that catalyzes the hydrolysis of an ester, for example an esterase or a lipase, to selectively cleave the 3-acyl group of one enantiomer without affecting the other. Alternatively, the racemic mixture may be first subjected to base-catalyzed hydrolysis to remove the 3-acyl group and to generate a racemic mixture of the corresponding 3-hydroxy β-lactam; the racemic mixture of 3-hydroxy β-lactam is then contacted with an enzyme capable of catalyzing acylation of an hydroxy group to selectively acylate the hydroxy group of one enantiomer without affecting the other. Or the racemic mixture of 3-hydroxy β-lactam may be acylated with a chiral carboxylic acid, and the resulting diastereomeric mixture may then be separated using methods known in the art, and the chiral auxiliary removed to provide the desired enantiomer. The enantiomerically pure N-unsubstituted-2-azetidinone may then be derivatized to an N-acyl-3-protected hydroxy-substituted-2-azetidinone which is used to acylate a baccatin III derivative to generate a taxol derivative.

Alternatively, the racemic mixture of (IIa) and (IIb) may be converted to a racemic mixture of N-acyl-3-protected hydroxy-4-substituted- 2-azetidinone according to the procedure disclosed in e.g. U.S. Pat. No. 5,175,315; this racemic mixture may be used directly to react with a 13-metal alkoxide, e.g. lithium alkoxide, of baccatin III in accordance with the highly diastereoselective method disclosed in European Published Application 534,708 (published Mar. 31, 1993) to give taxol or derivatives thereof (III, wherein R may be for example phenyl or t-butyloxy, and $R^2$ is as above defined).

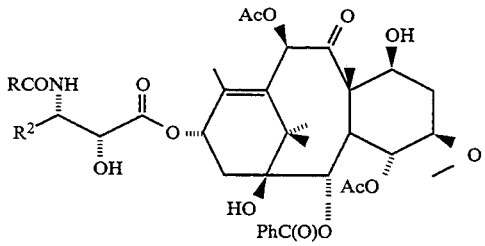

The utility of taxol (R=R²=phenyl) and taxotere (R=t-butyloxy, R²=phenyl) as antitumor agents are well known. The utility of other taxol derivatives of formula (III) as antitumor agents has been reported in European Published Application 534,708 (published Mar. 31, 1993)and PCT Published Application 92/09589 (published Jun. 11, 1992).

The following examples are illustrative of the invention and are not to be construed as limiting the scope of the invention in any manner.

Preparation of hydrobenzamide

To a 3 L 3-necked flask equipped with a mechanical stirrer and a thermometer was added 1 L of concentrated NH₄OH (ca 30%) (14.8 moles). A solution of benzaldehyde (265 g, 2.50 mol) in 500 mL of 2-propanol was added in one portion. The mixture was stirred vigorously at ca 22° C. for 43 hr. The resulting slurry was filtered and the filter cake was washed with water (1 L). After drying in vacuo, 242.4 g of hydrobenzamide was obtained as a white solid (mp 100°-102° C.) for a 97.4% yield.

The above procedure was followed to prepare the following bisoimines of the formula R²CH-(N=CHR²)₂:

hydrotoluamide (R²=4-methylphenyl),
hydroanisamide (R²=4-methoxyphenyl),
hydrofuramide (R²=2-furyl), and
hydrothienamide (R²=2-thienyl).

Example 1.
(±)-cis-3-Benzoyloxy-1-[phenyl(benzylideniminomethyl)]-4-phenylazetidin-2-one (1)

PhC(O)O\\\\\\   ,,,,Ph                    (1)
         \  /
          \/
      O=\  N
           \
            CH—N=CHPh
            |
            Ph

To a 100 mL, 3-neck flask equipped with a thermometer, dropping funnel and mechanical stirrer was added methylene chloride (23 mL) and hydrobenzamide (7.04 g, 0.024 moles). The solution was cooled (dry ice-acetone) to −20° C. under a dry argon atmosphere. Diisopropylethylamine (3.52 g, 0.027 moles) was added all at once. A solution of (benzoyloxy)acetyl chloride (prepared using the procedure of S. J. Danishefsky et al., J. Am. Chem. Soc. 1985, 107, 1280.) (5.16 g, 0.026 moles) in methylene chloride (13 mL) was added dropwise keeping the temperature at −20° to −15° C. (ca. 1.5 h). The mixture was stirred another hour at −20° C. then was diluted with deionized water (13 mL) (exotherm to 0° C.). The organic phase was separated and washed with water (2×10 mL), dried (anhyd. MgSO₄) and evaporated under vacuum to dryness giving crude title compound as a viscous oil (11.97 g) consisting of two diastereomers (ca. 1:1).

A sample of this material (2.97 g) was purified by column chromatography using a magnesia-silica stationary phase (Florosil ®, Fluka Chemie AG) and eluting with 20% EtOAc-n-hexane. The central product fractions were combined and evaporated to dryness giving a white solid (0.803 g). This material was recrystallized from EtOAc (5 mL)-n-hexane (10 mL) affording the product as a white solid (0.330 g) consisting of two diastereomers (96:4).

Purity (HPLC area): 98.3%; NMR (200 MHz, CDCl₃): δ=8.49 (s, 1H, N=CH); 7.68–7.17 (m, 20H, Ar); 6.34 (s, 1H, NCH); 6.06 (d, 1H, J=4.9 Hz, H-3); 4.85 (d, 1H, J=4.9 Hz, H-4); IR (KBr): ν (cm⁻¹)=1760 (C=O β-lactam), 1730 (C=O, ester); 1640 (C=N). El. anal. calc'd. for $C_{30}H_{24}N_2O_3$ (460.53): C, 78.24; H, 5.25; N, 6.08. Found: C, 77.96; H, 5.24; N, 6.12.

Example 2. (±)
cis-3-Benzoyloxy-4-phenylazetidin-2-one (2)

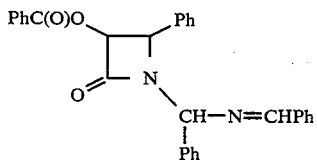

The remainder of the crude 1 (9.00 g) was dissolved in EtOAc (90 mL). To this solution was added a solution of sodium bisulfite (9.00 g, 58.5% min. SO₂, as mixture of bisulfite and metabisulfite) in water (45 mL) and the resulting biphasic mixture was heated to 50° C. The mixture was vigorously stirred at 50° C. until TLC (SG 60 F₂₅₄; 50% EtOAc-n-hexane; UV₂₅₄) confirmed completion of the reaction (4 h). The biphasic solution was separated in a separatory funnel. The organic phase was separated, washed with water (40 mL), dried (anhyd. MgSO₄), and evaporated under vacuum to dryness. The solid residue (2.25 g) was recrystallized from EtOAc (8 mL) giving the title compound as a white solid (3.55 g, 74.9% overall from hydrobenzamide), mp 118°-9° C. Purity (HPLC area): 99.4%; NMR (200 MHz, CDCl₃): δ=7.68–7.21 (m, 10H, Ar); 6.49 (br s, 1H, NH); 6.18 (dd, 1H, J=4.8, 2.7 Hz, H-3); 5.15 (d, 1H, J=4.8 Hz, H-4). IR (KBr): ν (cm⁻¹)=3260(NH); 1755 (C=O β-lactam), 1730 (C=O, ester). El. Anal. calc'd. for $C_{16}H_{13}NO_3$ (267.28): C, 71.90; H, 4.90; N, 5.24. Found: C, 71.76; H, 4.93; N, 5.31.

Example 3.
(±)-cis-3-Chloroacetoxy-1-[(phenyl)(benzylideniminomethyl)]-4-phenylazetidin-2-one (3)

ClCH₂C(O)O\\\\\\   ,,,,Ph                    (3)
          \  /
           \/
       O=\  N
            \
             CH—N=CHPh
             |
             Ph

To a 250 mL, 3-neck flask equipped with a thermometer, dropping funnel and mechanical stirrer was added methylene chloride (90 mL) and hydrobenzamide (22.38 g, 0.082 moles). The solution was cooled (dry ice-acetone) to −20° C. under a dry argon atmosphere. Diisopropylethylamine (11.19 g, 0.087 moles) was added all at once. A solution of chloroacetoxyacetyl chloride (prepared using the procedure of R. Lattrell and G. Lohaus, Liebigs Ann Chem, 1974, 870–900) (14.10 g, 0.082 moles) in methylene chloride (50 mL) was added dropwise keeping the temperature at −20° to −15° C. (ca. 2 h). The mixture was stirred another hour at −15° C. then was diluted with deionized water (100 mL) (exotherm to 0° C.). The organic phase was separated and washed with water (2×25 mL), dried (anhyd. MgSO4) and evaporated under vacuum to dryness giving crude title compound as a viscous oil (38.00 g) consisting of two diastereomers (ca. 1:1).

A sample of this material (3.22 g) was purified by column chromatography using a magnesia-silica stationary phase (Florosil®) and eluting with 20% EtOAc-n-hexane. The central product fractions were combined and evaporated to dryness giving a yellow oil (0.480 g). This material was crystallized from EtOAc (3 mL)-n-hexane (10 mL) affording the product as a white solid (0.310 g), consisting of two diastereomers (70:30). Purity (HPLC area): 98.6%; NMR (200 MHz, CDCl3): δ=8.45 (s, 1H, N=CH); 7.92–6.99 (m, 15H, Ar); 6.28, 6.23 (two diastereomers) (2s, 1H, NCH); 5.88, 5.82 (two diastereomers) (2d, 1H, J=4.8 Hz, H-3); 5.35, 4.80 (two diastereomers) (2d, 1H, J=4.8 Hz, H-4); 3.57 (q, 2H, J=15.4, CH2). IR (KBr): ν (cm$^{-1}$)=1760 (C=O β-lactam and ester); 1650 (C=N). El. anal. calc'd. for C25H21ClN2O3 (432.90): C, 69.42; H, 4.90; Cl, 8.09; N, 6.48. Found: C, 69.27; H, 4.89; Cl, 8.40; N, 6.39.

Example 4.
(±)-cis-3-Chloroacetoxy-4,phenylazetidin-2-one (4)

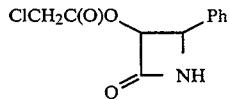

Part of the crude 3 (4.26 g) was dissolved in CH2Cl2 (22 mL). To this solution was added glacial acetic acid (4.60 mL) and deionized water (1.46 mL) and the resulting solution was heated to reflux. The mixture was vigorously stirred at reflux until TLC (SG 60 F254; 50% EtOAc-n-hexane; UV254) confirmed completion of the reaction (4 h). The solution was neutralized (pH 7.2) with dropwise addition of (17 mL) aq. NaOH (3.75 N) at 5°–10° C. The phases were separated and the aqueous phase was discarded. The organic phase was washed with aq. sodium bisulfite (25 mL, 10% wt.), dried (anhyd. MgSO4), and evaporated under vacuum to dryness. The solid residue (2.30 g) was recrystallized from toluene (10 mL) giving the title compound as a tan solid (0.727 g, 36.1% overall from hydrobenzamide). Purity (HPLC area): 91.4%. NMR (200 MHz, CDCl3): δ=7.41–7.27 (m, 5H, Ar); 6.43 (br s, 1H, NH); 5.94 (dd, 1H, J=2.7, 4.7 Hz, H-3); 5.09 (d, 1H, J=4.7 Hz, H-4); 3.62 (q, 2H, J=15.3, CH2).

Example 5.
(±)-cis-3-Acetyloxy-1-[(phenyl)(benzylidenimino)methyl]-4-phenylazetidin-2-one (5)

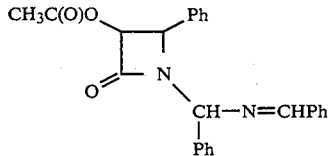

To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxyacetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous NH4Cl (sat) (150 mL, 100 mL), aqueous NaHCO3 (sat) (120 mL) and brine (120 mL). For purposes of characterization, the title compound can be isolated at this stage by drying the organic phase over MgSO4, filtering, and removing the solvent in vacuo. This provided the desired product in quantitative crude yield as a red glass. HPLC purity (area): 87.9% (1:1 mixture of diastereomers); $^1$H NMR (CDCl3, 200 MHz): δ=8.45 (s, 1H, N=CH), 7.80–7.85 (m, 1H, Ph), 7.60–7.65 (m, 1H, Ph), 7.26–7.50 (m, 9H, Ph), 7.00–7.10 (m, 4H, Ph), 6.28 (s, 0.5H, NCHN), 6.23 (s, 0.5H, NCHN), 5.81 (d, J=4.8 Hz, 0.5 H, H-3), 5.76 (d, J=4.8 Hz, 0.5H, H-3), 5.30 (d, J=4.8 Hz, 0.5 H, H-4), 4.75 (d, J=4.8 Hz, 0.5 H, H-4), 1.63 (s, 3H, CH3CO); IR (KBr): ν (cm$^{-1}$ )=1763 (C=O), 1641 (C=N); UV (methanol): λ max (nm)=216, 252.

Example 6.
(±)-cis-3-Acetyloxy-4-phenylazetidin-2-one (6)

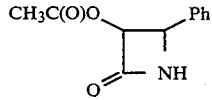

The solution of the compound of Example 5 in ethyl acetate (500 mL) from above was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite® (diatomaceous earth, Johns Manville). The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous NaHCO3 (sat) (300 mL) and brine (250 mL). The organic layer was dried over MgSO4, filtered and concentrated in vacuo to a final volume of 75 mL. This mixture was cooled to 4YX and the precipitated product isolated by filtration. The filter cake was washed with hexane (200 mL) to provide 16.12 g (78.1% overall yield from hydrobenzamide) of the title compound as white needles. mp =150°–151° C.; HPLC purity (area): 99.8%; $^1$H NMR (CDCl3, 200 MHz): δ=7.30–7.38 (m, 5H, Ph), 6.54 (br s, exchangeable, 1H, NH), 5.87 (dd, J=2.7, 4.7 Hz, 1H, H-3), 5.04 (d, J=4.7 Hz, 1H, H-4), 1.67 (s, 3H, CH3CO); IR (KBr): ν (cm$^{-1}$)=3210 (N-H), 1755, 1720

(C═O); KF: 0.17%; El. Anal. Calcd. for $C_{11}H_{11}NO_3$: C, 64.38; H, 5.40; N, 6.83; Found: C, 64.07; H, 5.34; N, 6.77.

Example 7.
(±)-cis-3-iso-Butyryloxy-1-[(phenyl)(benzylidenimino)methyl]-4-phenylazetidin-2-one (7)

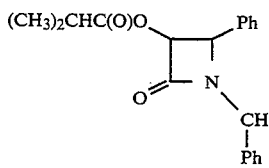

(7)

The title compound was prepared according to the procedure described in Example 5 except that iso-butyryloxyacetyl chloride was used instead of acetoxyacetyl chloride. Thus, hydrobenzamide (30.00 g, 100.5 mmol), triethylamine (16.8 mL, 121 mmol) and iso-butyryloxyacetyl chloride [18.9 g, 115 mmol, prepared by the procedure of Benington and Morin, J. Org. Chem., 26, 194 (1961)] yielded 50.65 g (118.8%) of the title compound as a dark orange syrup. For purposes of characterization, a portion (4.65 g) was purified by Florisil ®chromatography (25:75 ethyl acetate/hexane) to provide the title compound as a yellow syrup. Obtained as a 1:1 mixture of diastereomers; 1H NMR (CDCl$_3$, 200 MHz): δ=8.47 (s, 0.5H, N═CH), 8.46 (s, 0.5H, N═CH), 7.80–7.91 (m, 2H, Ph), 7.29–7.68 (m, 9H, Ph), 6.94–7.11 (m, 4H, Ph), 6.29 (s, 0.5H, NCHN), 6.25 (s, 0.5H, NCHN), 5.81 (d, J=4.9 Hz, 0.5H, H-3), 5.75 (d, J=4.8 Hz, 0.5H, H-3), 5.32 (d, J=4.9 Hz, 0.5H, H-4), 4.76 (d, J=4.8 Hz, 0.5H, H-4), 2.20 (p, J=7.0 Hz, 1H, CH(CH$_3$)$_2$), 0.80 (d, J=7.0 Hz, 3H, CH(CH$_3$)$_2$), 0.56 (d, J=7.0 Hz, 1.5H, CH(CH$_3$)$_2$), 0.54 (d, J=7.0 Hz, 1.5H, CH(CH$_3$)$_2$); IR (film): ν (cm$^{-1}$)=1771, 1748 (C═O), 1646 (C═N); UV (methanol): λ max (nm)=220, 254.

Example 8.
(±)-cis-3-(iso-Butyryloxy)-4-phenylazetidin-2-one (8)

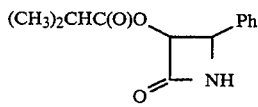

(8)

The title compound was prepared according to the procedure described in Example 6 except that wet catalyst was used and the reaction was performed on the 90.8 mmol scale based on the original amount of hydrobenzamide. Thus, the crude product of Example 7 (46.0 g) was re-dissolved in ethyl acetate (460 mL) and added to wet 10% palladium on activated charcoal (6.00 g of catalyst and 6 mL of water) to provide 10.35 g of the title compound (48.9% corrected overall yield from hydrobenzamide) as white crystals. mp=121°–122° C.; HPLC purity (area): 99.6%; 1H NMR (CDCl$_3$, 200 MHz): δ=7.27–7.39 (m, 5H, Ph), 6.33 (br s, exchangeable, 1H, NH), 5.87 (dd, J=2.6, 4.7 Hz, 1H, H-3), 5.05 (d, J=4.7 Hz, 1H, H-4), 2.24 (p, J=7.0 Hz, 1H, CH(CH$_3$)$_2$), 0.83 (d, J=7.0H, 3H, CH(CH$_3$)), 0.58 (d, J=7.0H, 3H, CH(CH$_3$)); IR (KBr): ν (cm$^{-1}$)=3203 (N-H), 1778, 1739 (C═O).

Example 9.
(±)-cis-3-Acetyloxy-1-[(4'-methylphenyl)(4'-methylbenzylidenimino)methyl]-4-(4'-methylphenyl)azetidin-2-one (9)

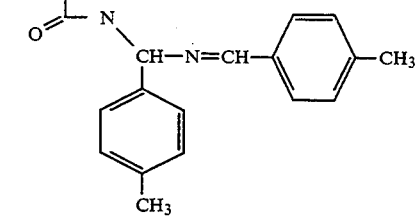

(9)

The title compound was prepared according to the procedure described in Example 5 except that hydrotoluamide was used instead of hydrobenzamide. Thus, hydrotoluamide (34.05 g, 100.0 mmol), triethylamine (20.9 mL, 150 mmol) and acetoxyacetyl chloride (18.9, 135 mmol) gave 52.0 g (118%) of the title compound as a brown syrup. For purposes of characterization, a portion (5.2 g) was purified by Florisil ® chromatography (25:75 ethyl acetate/hexane) to provide the title compound as a white solid. mp=110°–128° C.; HPLC purity (area): 97.8% (1:1 mixture of diastereomers); 1H NMR (CDCl$_3$, 200 MHz): δ=8.36 (s, 1H, N═CH), 7.75–7.80 (m, 1H, Ar), 7.53–7.56 (m, 1H, Ar), 7.06–7.35 (m, 7H, Ar), 6.81–6.90 (m, 3H, Ar), 6.19 (s, 0.5H, NCHN), 6.15 (s, 0.5H, NCHN), 5.79 (d, J=4.8 Hz, 0.5H, H-3), 5.73 (d, J=4.8Hz, 0.5H, H-3), 5.27 (br s, 0.5H, H-4), 4.77 (br s, 0.5H, H-4), 2.40 (s, 1.5H, PhCH$_3$), 2.39 (s, 1.5H, PhCH$_3$), 2.35 (s, 3H, PhCH$_3$), 2.24 (s, 1.5H, PhCH$_3$), 2.20 (s, 1.5H, PhCH$_3$), 1.661 (s, 1.5H, CH$_3$CO), 1.658 (s, 1.5H, CH$_3$CO); IR (KBr): ν (cm$^{-1}$)=1763, 1751 (C═O), 1635 (C═N); UV (methanol): λ max (nm) =214, 260.

Example 10.
(±)-cis-3-(Acetyloxy)-4-(4'-methylphenyl)azetidin-2-one (10)

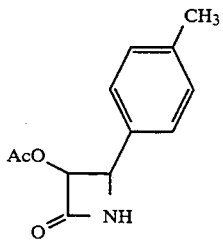

(10)

Method 1: Hydrogenation

The title compound was prepared according to the procedure described in Example 6 except that wet catalyst was used and the reaction was performed on the 45 mmol scale based on the original amount of hydrotoluamide. Thus, the crude product of Example 9 (23.4 g) in ethyl acetate (315 mL) was added to wet 10% palladium on activated charcoal (3.00 g of catalyst and 3 mL of water). This gave 3.50 g (35.5% corrected overall yield from hydrotoluamide) of the title compound as a white fluffy solid.

Method 2: Bisulfite

To the crude product of Example 9 (23.4 g) in ethyl acetate (315 mL) was added water (75 mL) and sodium bisulfite (35 g). This biphasic mixture was vigorously stirred at 50° C. for 23 h and the organic and aqueous layers were separated. The organic layer was washed with water (50 mL) and brine (150 mL), dried over MgSO4, and concentrated in vacuo to 30 mL. The mixture was cooled to 5° C. and the precipitated title compound isolated by filtration and rinsed with cold ethyl acetate (10 mL). This provided 4.27 g (43.3% corrected overall yield from hydrotoluamide) of the title compound as a white solid. mp=130°–131° C.; HPLC purity (area): 98.6%; 1H NMR (CDCl3; 200 MHz): δ=7.13–7.22 (m, 4H, Ar), 6.29 (br s, exchangeable, 1H, NH), 5.85 (dd, J=2.6, 4.7 Hz, 1H, H-3), 5.00 (d, J=4.7 Hz, 1H, H-4), 2.35 (s, 3H, PhCH3), 1.70 (s, 3H, CH3CO); IR (KBr); ν (cm$^{-1}$)=3192 (N-H), 1778, 1752 (C=O); UV (methanol): λ max (nm)=222, 266.

Example 11.
(±)-cis-3-Acetyloxy-1-[(4'-methoxyphenyl)(4'-methoxybenzylidenimino)methyl]-4-(4'-methoxyphenyl)azetidin-2-one (11)

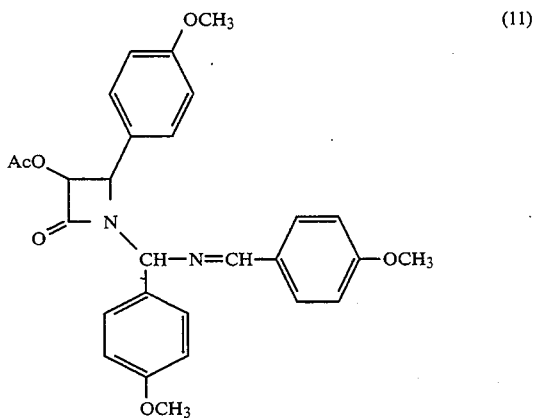

The title compound was prepared according to the procedure described in Example 5 except that hydroanisamide was used instead of hydrobenzamide and the reaction was performed on 12.9 mmol (vs 100 mmol) scale. Thus, hydroanisamide (5.00 g, 12.9 mmol), triethylamine (2.15 mL, 15.4 mmol) and acetoxyacetyl chloride (1.59 mL, 14.8 mmol) gave 6.38 g (101.2%) of the title compound as a pale red syrup. Obtained as a 1:1 mixture of diastereomers; 1H NMR (CDCl3; 200 MHz): δ=8.34 (s, 0.5H, N=CH), 8.33 (s, 0.5H, N=CH), 7.75 (d, J=8.8 Hz, 0.5H, Ar), 7.58 (d, J=8.7 Hz, 0.5H), 7.14–7.27 (m, 3H, Ar), 6.78–7.03 (m, 6H, Ar), 6.63 (d, J=2.6 Hz, 1H, Ar), 6.58 (d, J=2.5 Hz, 1H, Ar), 6.15 (s, 0.5H, NCHN), 6.11 (s, 0.5H, NCHN), 5.75 (d, J=4.8 Hz, 0.5H, H-3), 5.69 (d, J=4.7 Hz, 0.5H, H-3), 5.21 (d, J=4.8 Hz, 0.5 H, H-4), 4.69 (d, J=4.7 Hz, 0.5H, H-4), 3.89 (s, 3H, PhOCH3), 3.85 (s, 3H, PhOCH3), 3.81 (s, 1.5H, PhOCH3), 3.79 (s, 1.5H, PhOCH3), 1.68 (s, 1.5H, CH3CO), 1.67 (s, 1.5H, CH3CO); UV (methanol): λ max (nm)=216, 252.

Example 12.
(±)-cis-3-(Acetyloxy)-4-(4'-methoxyphenyl)azetidin-2-one (12)

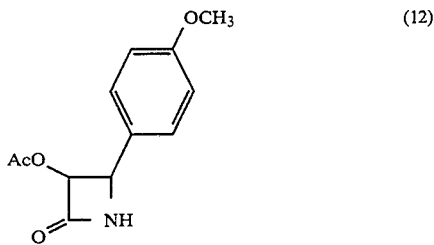

The title compound was prepared according to the procedure described in Example 6 except that the product was isolated by preparative TLC and the reaction was performed on 12.9 mmol scale based on the original amount of hydroanisamide. Thus, the crude product of Example 11 (6.38 g) was re-dissolved in ethyl acetate (80 mL) and added to 10% palladium on activated charcoal (1.00 g). This gave 4.277 g (141%) of a crude solid. A portion (200 mg) was purified by preparative TLC (2 mm silica gel; 1:1 ethyl acetate/hexane) to provide the 160 mg (75.5% corrected overall yield from hydroanisamide) of the title compound as a slightly yellow powder. This was recrystallized from methylene chloride/hexane. mp=110°–111° C.; HPLC purity (area): 99.7%; 1H NMR (CDCl3; 200 MHz): δ=7.24 (d, 9.0 Hz, 2H, Ar), 6.89 (d, J=8.7 Hz, 2H, Ar), 6.23 (br s, exchangeable, 1H, NH), 5.83 (dd, J=2.7, 4.6 Hz, 1H, H-3), 4.99 (d, J=4.6 Hz, 1H, H-4), 3.81 (s, 3H, PhOCH3), 1.73 (s, 3H, CH3CO); IR (KBr): ν (cm$^{-1}$)=3218 (N-H), 1751, 1728 (C=O); UV (methanol): λ, max (nm)=208, 230, 276.

Example 13.
(±)-cis-3-Acetyloxy-1-[(2'-furyl)(2'-furylmethylenimino)methyl]-4-(2'-furanyl)azetidin-2-one (13)

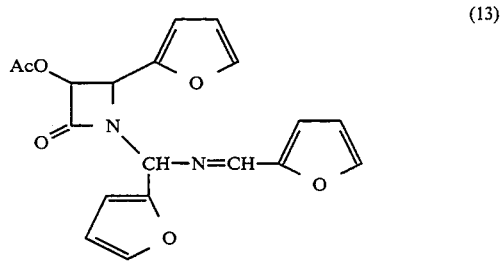

The title compound was prepared according to the procedure described in Example 5 except that hydrofuramide was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (90.4%) of the title compound as a pale red syrup. Obtained as a 1:1 mixture of diastereomers; 1H NMR (CDCl3; 200 MHz): δ=8.211 (s, 0.5H, N=CH), 8.208 (s, 0.5H, N=CH), 7.14–7.59 (m, 3H, furyl), 6.90 (d, J=3.5 Hz, 0.5H, furyl), 6.83 (d, J=3.5 Hz, 0.5H, furyl), 6.10–6.53 (m, 6H, furyl, NCHN), 5.90 (d, J=4.9 Hz, 0.5H, H-3), 5.86 (d, J=4.8 Hz, 0.5H, H-3), 5.35 (d, J=4.8 Hz, 0.5H, H-4), 4.90 (d, J=4.9 Hz, 0.5H, H-4), 1.91 (s, 1.5H, CH3CO),1.88 (s, 1.5H, CH3CO); IR (film): ν (cm$^{-1}$)=1778, 1753

Example 14.
(±)-cis-3-(Acetyloxy)-4-(2'-furanyl)azetidin-2-one (14)

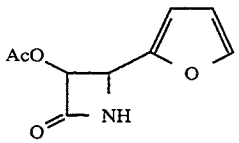

(14)

The title compound was prepared according to the procedure described in Example 6 except that the product was isolated by preparative TLC and the reaction was performed on the 2.7 mmol scale based on the original amount of hydrofuramide. Thus, the crude product of Example 13 (1.00 g) was re-dissolved in ethyl acetate (50 mL) and added to 10% palladium on activated charcoal (150 mg). Purification of the crude solid by preparative TLC (2 mm silica gel, 1:1 ethyl acetate/hexane) gave 386 mg (65.8% corrected overall yield from hydrofuramide) of the title compound as a yellow solid. This was recrystallized from ethyl acetate/hexane. mp=118°–119° C.; HPLC purity (area): 99.4%; $^1$H NMR (CDCl$_3$, 200 MHz): δ=7.44 (t, J=1.3 Hz, 2H, furyl), 6.39 (d, J=1.3 Hz, 1H, furyl), 6.21 (br s, exchangeable, 1H, NH), 5.88 (dd, J=2.2, 4.6 Hz, 1H, H-3), 5.05 (d, J-4.6 Hz, 1H, H-4), 1.92 (s, 3H, CH$_3$CO); IR (KBr): ν (cm$^{-1}$)=3203 (N-H), 1756, 1726 (C=O); UV (methanol): λ max (nm)=222.

Example 15.
(±)-cis-3-Acetyloxy-1-[(2'-thienyl)(2'-thienylmethylenimino)methyl]-4-(2'-thienyl)azetidin-2-one (15)

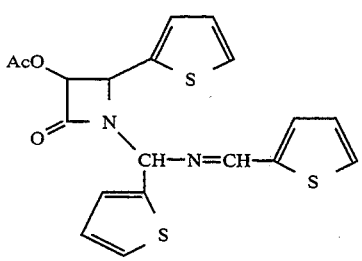

(15)

The title compound was prepared according to the procedure described in Example 5 except that hydrothienamide was used instead of hydrobenzamide. Thus, hydrothienamide (30 g, 94.7 mmol), triethylamine (15.84 mL, 114 mmol) and acetoxyacetyl chloride (11.6 mL, 108 mmol) provided the title compound as viscous oil. The product obtained contained a mixture of diastereomers. $^1$H NMR (CDCl$_3$): δ8.52 (s, 1H), 8.502 (s, 1H), 7.51 (d, J=4.9 Hz, 1H), 7.45 (d, J=4.4 Hz, 1H), 7.41 (d, J=3.1 Hz, 1H), 7.37 (d, 1H), 7.30 (m, 3H), 7.16 (m, 1H), 7.16 (m, 3H), 7.09 (m, 2H), 6.94 (m, 1H), 6.89 (m, 1H), 6.81–6.74 (m, 4H), 6.48 (s, 1H), 6.43 (s, 1H), 5.85 (m, 2H), 5.59 (d, J=4.8 Hz, 1H), 5.17 (d, J=4.8 Hz, 1H), 1.87 (s, 3H), 1.86 (s, 3H).

Example 16.
(±)-cis-3-(Acetyloxy)-4-(2'-thienyl)azetidin-2-one (16)

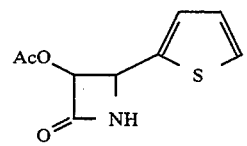

(16)

A 70% aqueous solution of acetic acid (0.35 mL glacial acetic acid and 0.15 mL water) was added in one portion to a stirred solution of 15 (0.431 g, 1.03 mmol), dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichloromethane, and then placed on a silica gel column measuring 4" by 0.5". Elution using a gradient of 10 through 60% EtOAc/hexane provided less polar sideproducts and then the title compound (0.154 g, 75%) as a white solid. $^1$H NMR (CDCl$_3$): δ7.32 (dd, J=4.7, 1.5 Hz, 1H), 7.03 (m, 2H), 6.75 (bs, 1H), 5.86 (dd, J=4.6, 2.7 Hz, 1H), 5.27 (d, J=5.3 Hz, 1H), 1.83 (s, 3H). $^{13}$C NMR (CDCl$_3$): δ169.3, 165.5, 138.4, 127.1, 127.07, 126.2, 78.3, 54.0, 20.0.

Example 17.
(±)-cis-3-Acetyloxy-4-phenylazetidin-2-one (6)-hydrogenolysis

To a 2.0 L 3-necked flask equipped with a thermometer, pressure equalizing dropping flask and mechanical stirrer was added methylene chloride (500 mL), hydrobenzamide (100.00 g, 0.335 mol) and triethylamine (56.0 mL, 0.402 mol). This mixture was cooled under a stream of argon to 4° C. using an ice-bath at which point a solution of acetoxyacetyl chloride (41.35 mL, 0.385 mmol) in methylene chloride (1000 mL) was added dropwise over a period of 1 hour. After an additional hour, the stirring was discontinued and the reaction flask moved to the cold room (4° C.) for a further 15 hours at which point TLC analysis demonstrated complete reaction. The reaction mixture was transferred to a 4 L separatory funnel and washed twice with aqueous NH$_4$Cl (sat) (500 mL, 250 mL). The organic phase was then washed successively with aqueous NaHCO$_3$ (sat) (400 mL) and aqueous NaCl (sat) (250 mL), dried over MgSO$_4$ (ca.100 g), filtered and concentrated by rotovap (bath T=40° C.). The remaining viscous oil was further dried by pumping for 1 day at 2 Torr whereupon the oil solidified to furnish a red glass (136.88 g, 102.5%) which was used without further purification.

The crude solid from above (136.88 g) was dissolved in 800 mL of ethyl acetate and transferred, under a stream of argon, to a 2.0 L Parr flask containing 20.0 g of 10% palladium on activated carbon (Aldrich). This mixture was treated with hydrogen (4 atm) for 1 day at 23° C. and the catalyst removed by filtration through Whatman filter paper using a Buchner funnel. The filter cake was reslurried in ethyl acetate (500 mL), stirred (10 min) and re-filtered. This procedure was repeated. The filter cake was rinsed with 100 mL of ethyl acetate and the flitrates combined. The organic layer was then washed with 1N HCl (500 mL) and both layers filtered through Whatman filter paper to remove the white precipitate which was rinsed with ethyl acetate (100 mL). The organic and aqueous layers were then separated and the organic layer was washed with another portion of 1N HCl (250 mL). The combined 1N HCl washes were re-extracted with ethyl acetate (500 mL) and the organic layers were combined and subsequently washed with aqueous NaHCO$_3$ (sat) (500 mL) and aqueous NaCl (sat) (300 mL). The organic layer was dried over MgSO$_4$ (ca. 100 g), filtered and concentrated in vacuo to 250 mL. The mixture was cooled to 4° C. (overnight in cold room) and the precipitated solid isolated by filtration through Whatman filter paper. The filter cake was washed with hexane (200 mL) to provide, after drying in vacuo, pure (±) cis-3-acetyloxy-4-phenylazetidin-2-one (49.97 g, 72.7%) as white needles (mp 150°–151° C.).

Example 18.
(±)-cis-3-acetyloxy-4-phenylazetidin-2-one (6)-hydrolysis with 70% acetic acid A dry 1-L three-neck round-bottom flask under an inert atmosphere (N$_2$) was charged with hydrobenzamide (100.0 g, 335 mmol, 1.00 equiv) and methylene chloride (333 mL). The solution was cooled to 5° C. and diisopropylethylamine (61.3 mL, 352 mmol, 1.05 equiv) was added in one portion. The reaction was further cooled to −20° C. and the temperature maintained with a constant temperature bath. Separately, acetoxyacetyl chloride (36.0 mL, 335 mmol, 1.00 equiv) and methylene chloride (167 mL) were mixed and transfered to an addition funnel (total volume: 203 mL). This solution was added over a 2 h 10 min period to the previously prepared hydrobenzamide solution. The rate was adjusted such that the temperature did not warm past −16° C. The light brown reaction mixture was stirred for 1 h at −20° C. Aliquots of the reaction mixture (100 µL) were removed 5 min and 30 min after the addition of acetoxyacetyl chloride. If the reaction mixture contained >5% hydrobenzamide (by area) after 30 min, additional diisopropylethylamine (6.13 µL, 35.2 mmol, 0.105 equiv) was added to the reaction mixture, followed by a solution of acetoxy acetyl chloride (3.60 mL, 33.5 mmol, 0.10 equiv) in methylene chloride (15 mL). After reaction was complete, deionized water (333 mL) was added and the mixture was stirred for 5 min. The phases were separated and the reaction vessel was rinsed with methylene chloride (110 mL). The methylene chloride rinse was used to extract the aqueous phase. The organic phases were combined (total volume: 750 mL). The aqueous phase was discarded.

The rich organic stream was transferred to a 2-L round bottom flask fitted with a reflux condenser and overhead stirrer. To the stirred solution was added 70% aqueous acetic acid (156 mL). Total reaction volume was ca. 906 mL. The solution was warmed to reflux. Pot temperature was 42°–45° C. Although the reaction was complete after 8 h, heating was continued for 16 h. The reaction mixture was cooled to 10° C. The pH of the reaction mixture was adjusted from 5.10 to 7.10 by the addition of aqueous NaOH solution (3.75 N, 440 mL) while the temperature was kept below 20° C. The reaction mixture was transferred to a 4-L Erlenmeyer flask and aqueous sodium metabisulfite (1100 mL, 10% w/v) was added in one portion. The reaction mixture was stirred for 10 min at 30° C. The phases were separated and the rich methylene chloride stream was concentrated in vacuo (25 mm Hg, 30° C. bath temperature) to 200 mL. The addition of ethyl acetate and concentration were repeated. The resulting slurry was stirred for 2–3 h at −5° C. The solid was collected by vacuum filtration (15 cm diam. filter). The density of the product was approx. 3 mL per g. The product was washed with cold (5° C.) ethyl acetate (100 mL). The product was dried to a constant weight (1.0 mm Hg, 25° C., 5h) and (49.3 g, 240 mmol, 71.7% weight yield) was recovered as off-white needles with a purity of 100.8% by HPLC.

Example 19.
(±)-cis-3-Acetyloxy,4-phenylazetidin-2-one (6)-hydrolysis with aqueous sodium bisulfite

A.1. Cycloaddition in Ethyl Acetate

To a 2 L, 3-neck flask equipped with a thermometer, dropping funnel and mechanical stirrer was added ethyl acetate (500 mL) and hydrobenzamide (50.00 g, 0.167 moles). The solution was cooled (ice bath) to 0° C. under a dry argon atmosphere. Triethylamine (19.50 g, 0.193 moles) was added all at once. A solution of acetoxyacetyl chloride (24.02 g, 0.176 moles) in ethyl acetate (20 mL) was added dropwise keeping the temperature at 0°–5° C. (ca. 1.5 h). The mixture was stirred another 2 h at 0° C. then stored 17 h in the cold room (ca. 5° C.). The mixture was diluted with deionized water (250 mL) with cooling (exotherm to 10° C.). After vigorous stirring, the aqueous phase was separated and extracted with more ethyl acetate (100 mL). The organic phases were combined and the resulting solution of crude 3-acetoxy-1-[(phenyl)(benzylidenimino)methyl]-4-phenylazetidin-2-one was treated with aqueous bisulfite as described below in part B.

A.2. Cycloaddition in Methylene Chloride

To a 1 L, 3-neck flask equipped with a thermometer, dropping funnel and mechanical stirrer was added methylene chloride (166 mL) and hydrobenzamide (50.00 g, 0.167 moles). The solution was cooled (dry ice-acetone) to −20° C. under a dry argon atmosphere. Diisopropylethylamine (25.01 g, 0.193 moles) was added all at once. A solution of acetoxyacetyl chloride (25.14 g, 0.184 moles) in methylene chloride (91 mL) was added dropwise keeping the temperature at −20° to −15° C. (ca 1.5 h). The mixture was stirred another hour at −20° C. then was diluted with deionized water (166 mL) (exotherm to 0° C.). After vigorous stirring, the aqueous phase was separated and extracted with more methylene chloride (55 mL). The combined organic phases were coevaporated with ethyl acetate (400 mL) to remove the methylene chloride. The resulting ethyl acetate solution (ca. 450 mL) of crude 3-acetoxy-1-[(phenyl)(benzylidenimino)methyl]-4-phenylazetidin-2-one was treated with aqueous bisulfite as described below in part B.

B. Bisulfite Cleavage

To the ethyl acetate solution of crude 3-acetoxy-1-[(phenyl)(benzylidenimino)methyl]-4-phenylazetidin-2-one from part A.1. or A.2. was added deionized water (250 mL) and sodium bisulfite (75.00 g) and the resulting biphasic solution was vigorously stirred at 50°±2° C. until TLC confirmed completion of the reaction (3–4 h). The biphasic solution was separated. The aqueous phase (pH 6.0) was discarded and the organic phase was washed with water (150 mL), dried (MgSO$_4$), and concentrated on rot. evaporator (35° C.) to a volume of 100 mL. The thick slurry was cooled and stirred at 0°–5° C. for 2 h. The solid (white needles) was filtered on a Buchner, washed with cold ethyl acetate (25 mL), and dried in vacuo to constant weight.

The A.1. process afforded 20.63 g (60.0% overall) and the A.2. process afforded 22.94 g (66.7% overall) of (±)-cis-3-acetyloxy-4-phenylazetidin- 2-one; HPLC purity (area): 99.3% and 99.4%, respectively.

Example 20. (±)-cis-3-Acetoxy-4-phenylazetidin-2-one (6)-hydrolysis with 75% acetic acid A dry 1 L three-neck, round-bottom flask equipped with an overhead stirrer, addition funnel, septum and nitrogen inlet is charged with hydrobenzamide (100 g, 335 mmol, 1.00 equiv) and methylene chloride (333 mL). The solution is agitated at ca. 160 rpm and cooled to 5° C. Diisopropylethylamine (67.1 mL, 385.2 mmol, 1.15 equiv.) is added in one portion under nitrogen. The reaction mixture is further cooled to −20° C. and the temperature maintained with a constant temperature bath (−30° C.). Separately, acetoxyacetyl chloride (39.6 mL, 368.4 mmol, 1.10 equiv.) and methylene chloride (184 mL) are mixed at ambient temperature and transferred under nitrogen to the addition funnel and this solution is added over a 5 h period. The initial rate is adjusted such that the temperature remained below −16° C. The progress of the reaction is followed by HPLC. An aliquot of the reaction mixture (100 μL) is removed 10 min after addition of the acetoxyacetyl chloride solution is complete. The light brown reaction mixture is stirred at −20° C. until HPLC analysis shows <5% hydrobenzamide (area percent analysis). If the reaction mixture contains >5% hydrobenzamide by area, the reaction mixture is charged with additional diisopropylethylamine and acetoxyacetyl chloride. [As an example, if the mixture contained 10% hydrobenzamide, additional diisopropylethylamine (6.13 mL, 35.2 mmol, 0.105 equiv) is added neat, followed by a solution of acetoxyacetyl chloride (3.60 mL, 33.5 mmol, 0.10 equiv.) in methylene chloride (16.7 ml). The acetoxyacetyl chloride solution is added at the rate described above. The reaction mixture is stirred for 10 min at −20° C. and then sampled for HPLC analysis.] After the reaction is complete, water (333 mL) is added in one portion over ca. 10 sec. The temperature of the mixture increased to 5° C. The mixture is stirred for 5–10 min. The phases are separated at 5° C. (settling time <1 rain) and the reaction vessel rinsed with methylene chloride (100 mL). The methylene chloride rinse is used to extract the aqueous phase. The extraction is performed at ambient temperature. The organic phases are combined.

The rich organic stream is transferred to a 2 L three-neck, round-bottom flask fitted with a reflux condenser, overhead stirrer and stopper. To this stirred solution at ambient temperature is added acetic acid (150 mL, 7.9 equiv.), followed by water (50 mL, 8.28 equiv.). Addition time is ca. 20 sec and the total reaction volume is ca. 953 mL. The solution is warmed to reflux (pot temperature 42°–45° C.). An aliquot (100 μL) is taken every hour and analyzed by HPLC. The reaction is judged complete when the area percent of (±)-cis-3-acetyloxy-1-[(phenyl)(benzylidenimino)methyl]-4-phenylazetidin-2-one is <2%. The hydrolysis described in this procedure is complete in 4 h. The reaction mixture is cooled to 10°–15° C. The pH of the reaction mixture is adjusted from 4.64 to 6.92 by the addition of aqueous NaOH (3.75 N, 705 mL) while the temperature is kept between 10° C. and 20° C. The NaOH solution is added over 2 h. During neutralization of this mixture, the title compound partially precipitated and is redissolved by warming the solution to 25° C. The phases are separated at 25° C. (settling time <1 min) and the reaction vessel rinsed with methylene chloride (100 mL). The methylene chloride rinse is used to extract the aqueous phase. The combined rich methylene chloride stream (850 mL) is transferred to a 2 L three-neck round-bottom flask equipped with an overhead stirrer and cooled to −5° to 0° C. with stirring. The product partially precipitates out. Heptane (850 ml, equal to the volume of rich methylene chloride stream) is added during 1 h and the resulting slurry is stirred for an additional 1 h at −5° to 0° C. The solid title compound is collected by vacuum filtration (9 cm diam. filter), washed with cold (−5° to 0° C.) 10% methylene chloride in heptane (200 ml) and dried to a constant weight (24–25 in Hg, 35°–38° C., 12–15 h). The title compound (54.42 g, 77.7% weight yield) is recovered as off-white needles with a purity of 100% by HPLC.

Example 21. Alternative method for the preparation of (±)-cis-3-Acetyloxy-1-[(2'-furanyl)(2'-furanylmethylenimino)methyl]-4-(2'-furanyl)azetidin-2-one (13) and (±)-cis-3-(Acetyloxy)-4-(2'-furanyl)azetidin-2-one (14)

To a 2 L, 3-necked round bottom flask equipped with a thermometer, magnetic stirrer and dropping funnel was added hydrofuramide (80.48 g, 300 mmol) and ethyl acetate (1.0 L). With stirring and under a blanket of argon, the reaction mixture was cooled to 5° C. and triethylamine (50.2 mL, 360 mmol) was added. A solution of acetoxyacetyl chloride (37.0 mL, 344 mmol) in ethyl acetate (500 mL) was then added dropwise over a 1 h period. After 16 h at 5° C., the reaction mixture was allowed to warm to 20° C. (1.5 h) and transferred to a separatory funnel. The organic layer was washed with aqueous NH$_4$Cl (sat) (500 mL). Both layers were filtered through glass microfibre filter paper (Whatman) and the filter cake rinsed with ethyl acetate (50 mL). The flitrate was transferred back to the separatory funnel and the aqueous layer removed. The organic layer was then washed successively with aqueous NH$_4$Cl (sat) (250 mL), aqueous NaHCO$_3$ (sat) (400 mL) and brine (400 mL). The organic layer containing the title compound 13 was filtered through glass microfibre filter paper (Whatman).

The solution from above was divided into two equal portions (approximately 750 mL each) and these were carefully transferred, under a stream of argon, to two 2.0 L Parr flask each containing 10% palladium on activated charcoal (6.00 g). This mixture was treated with hydrogen (4 atm) for 1 d and the catalyst removed by filtration through a pad of Celite TM. The filter cake was rinsed with ethyl acetate (100 mL) and the flitrates combined. The organic layer was washed twice with 10% HCl (500 mL, 250 mL) and the combined 10% HCl washes were re-extracted with ethyl acetate (500 mL). The combined organic layers were washed with aqueous NaHCO$_3$ (sat) (400 mL) and brine (400 mL). The organic layer was dried over MgSO$_4$ and treated with activated decolorizing charcoal (30 g). After 15 min the mixture was filtered through a pad of Celite TM and concentrated in vacuo to a final volume of 160 mL. This mixture was cooled to 4° and the precipitated product isolated by filtration. The filter cake was washed with diethyl ether and hexane (100 mL of each)

to provide 35.98 g (61.4% overall yield form hydrofuramide) of the title compound 14 as white needles (mp 118°–119° C.). HPLC purity (area): 98.5%.

Example 22. Alternative method for the preparation of (±)-cis-3-acetyloxy-1-[(phenyl)(benzylidenimino)methyl]-4-phenylazetidin-2-one (5) and (±)-cis-3-acetyloxy-4-phenylazetidin-2-one (6)

To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxyacetyl chloride (12.4 mL, 115 mmol) in ethyl acetate (300 mL) was then added dropwise over a 90 min period. After 16 h at 5° C., the reaction mixture was allowed to warm to 20° C. (1.5 h) and transferred to a separatory funnel. The organic layer was washed successively with aqueous NH4Cl (sat) (150 mL, 75 mL), aqueous NaHCO3 (sat) (100 mL) and brine (75 mL).

To the above organic layer was added 90% aqueous formic acid (22.0 mL, 0.57 mol) and the mixture stirred at room temperature for 2 d. It was transferred to a separatory funnel and washed with water (200 mL) and aqueous NaHCO3 (sat) (200 mL) (add slowly). To the aqueous NaHCO3 (sat) washing, solid NaHCO3 was carefully added until the pH was 7.5. The organic layer was then washed with NaCl (sat), dried over MgSO4, filtered and concentrated in vacuo to 75 mL. This mixture was cooled to 4° C. and the precipitated product isolated by filtration. The filter cake was rinsed with hexane (200 mL) to provide 14.26 g (69.1% overall yield from hydrobenzamide) of the title compound 6 as white needles (mp=150°–151° C.). HPLC purity (area): 96.5%.

Example 23.
(±)-cis,3-(1'-phenethyloxy)-1-[(phenyl)(benzylidenimino)methyl]-4-phenylazetidin-2-one (23)

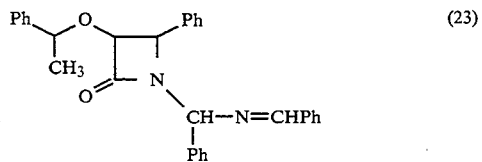

To a 100 mL, 3-necked round bottom flask equipped with thermometer, magnetic stirrer and dropping funnel was added hydrobenzamide (2.98 g, 10.0 mmol) and dichloromethane (15 mL). With stirring and under a blanket of argon, the reaction mixture was cooled to 5° C. and triethylamine (1.67 mL, 12.0 mmol) was added. A solution of (±)-phenethyloxyacetyl chloride (2.58 g, 13.0 mmol) in dichloromethane (30 mL) was then added dropwise over a 1 h period. After 16 h at 5° C., the reaction mixture was allowed to warm to 20° C. and transferred to a separatory funnel. The organic layer was washed successively with aqueous NH4Cl (sat) (30 mL, 15 mL), aqueous NaHCO3 (sat) (25 mL) and brine (25 mL). The organic layer was dried over MgSO4, filtered and the solvent removed in vacuo to provide 4.57 g (99.2%) of the title compound as a red, viscous oil. The product was obtained as a mixture of diastereomers. $^1$H NMR (CDCl3; 200 MHz): δ=8.443 (s, 0.25H, N=CH), 8.414 (s, 0.25H, N=CH), 8.406 (s, 0.5H, N∇CH), 7.77–7.91 (m, 2H, Ar), 6.82–7.69 (m, 18H, Ar), 6.28 (s, 0.25H, NCHN), 6.22 (s, 0.5H, NCHN), 6.17 (s, 0.25H, NCHN), 5.02 (d, J=4.4 Hz, 0.25H, H-3), 4.89 (d, J=5.0 Hz, 0.25H, H-3), 4.77 (d, J=5.0 Hz, 0.25H, H-3), 4.70 (d, J=4.9 Hz, 0.25H, H-3), 4.444.67 (m, 0.75H, H-4), 4.35 (d, J=5.0 Hz, 0.25H, H-4), 3.73–3.94 (m, 1H, MeCHPh), 1.51 (d, J=6.4 Hz, 0.75H, CH3CH), 1.33 (d, J=6.4 Hz, 0.75H, CH3CH), 1.32 (d, J=6.5 Hz, 0.75H, CH3CH), 0.89 (d, J=6.5 Hz, 0.75H, CH3CH).

Example 24.
(±)-cis-3-(1'-phenethyloxy)-4-phenylazetidin-2-one (24)

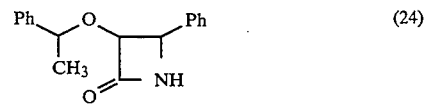

The solution of the compound of Example 23 in ethyl acetate (50 mL) was carefully transferred, under a stream of argon, to a 200 mL Parr flask containing 10% palladium on activated charcoal (0.60 g). This mixture was treated with hydrogen (4 atm) for 16 h whereupon the catalyst was removed by filtration through a pad of Celite ™. The filter cake was slurried in ethyl acetate (50 mL), stirred (10 min) and filtered. The filter cake was rinsed with ethyl acetate (10 mL) and the filtrates combined. The organic layer was washed with 10% HCl (50 mL) and both layers filtered through a sintered glass funnel to remove the white precipitate (dibenzylamine.HCl). The phases were separated and the organic layer was washed with another portion of 10% HCl (30 mL). The combined 10% HCl washes were re-extracted with ethyl acetate (100 mL). The combined organic layers were washed with aqueous NaHCO3 (sat) (50 mL) and brine (50 mL). The organic layer was dried over MgSO4, filtered and concentrated in vacuo to yield a yellow oil (2.967 g) which was purified by preparative TLC (2 mm silica gel, 3: 7 ethyl acetate/hexane) to yield 2.41 g (91%) of the title compound 24 as an oil and a mixture of diastereomers. $^1$H NMR (CDCl3; 200 MHz): δ=7.18–7.50 (m, 9H, Ar), 6.92–6.97 (m, 1H, Ar), 6.33 (br s, 0.5H, exchangeable, NH), 6.28 (br s, 0.5H, exchangeable, NH), 4.60–4.82 (m, 2H, H-3, H-4), 3.94 (q, J=6.5 Hz, 1H, CHCH3), 1.34 (d, J=6.5 Hz, 1.5H, CHCH3), 0.91 (d, J=6.5 Hz, 1.5H, CHCH3).

Example 25.
(±)-cis-3-(4',6'-di-O-acetoxy-2',3'-dideoxy-α-D-glucopyranosyloxy)-4-phenylazetidin-2-one (25)

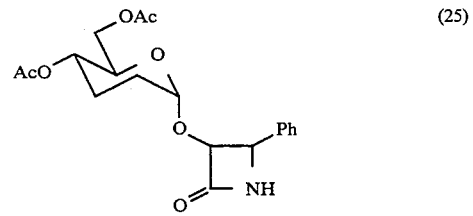

To a 50 mL, 3-necked round bottom flask equipped with a thermometer, magnetic stirrer and dropping funnel was added (4,6-di-O-acetoxy-2,3-dideoxy-α-D-glucopyranosyloxy)acetyl chloride (774 mg, 2.51 retool) and dichloromethane (20 mL) and the solution cooled to −78° C. and triethylamine (0.56 mL, 4.02 mmol) was added. After stirring 15 rain, a solution of hydrobenzamide (824 mg, 2.76 mmol) in toluene (5 mL) was added. The reaction mixture was warmed to 5° C. After 16 h at this temperature, the reaction was diluted with dichloromethane (50 mL) and transferred to a separatory funnel. The organic layer was washed successively with aqueous NH₄Cl (sat) (30 mL, 15 mL), aqueous NaHCO₃ (sat) (25 mL) and brine (25 mL). The organic layer was dried over MgSO₄, filtered and concentrated in vacuo to provide 1.435 g (100.2%) of (±)-cis-3-(4',6'-di-O-acetoxy-2',3'-dideoxy-α-D-glucopyranosyloxy)-1-[(phenyl)(benzylidenimino)methyl]-4-phenylazetidin-2-one as a viscous oil and mixture of diastereomers.

A solution of the above compound (1.435 g) in ethyl acetate (50 mL) was carefully transferred, under a stream of argon, to a 200 mL Parr flask containing 10% palladium on activated charcoal (315 mg). This mixture was treated with hydrogen (4 atm) for 16 h whereupon the catalyst was removed by filtration through a pad of Celite ™. The filter cake was slurried in ethyl acetate (50 mL), stirred (10 min) and filtered. The filter cake was rinsed with ethyl acetate (10 mL) and the flitrates combined. The organic layer was washed with 10% HCl (25 mL) and both layers filtered through a sintered glass funnel to remove the white precipitate (dibenzylamine-HCl). The phases were separated and the organic layer was washed with another portion of 10% HCl (25 mL), aqueous NaHCO₃ (sat) (25 mL) and brine (25 mL). The organic layer was dried over MgSO₄ filtered and concentrated in vacuo to yield a viscous oil (0.50 g). This oil was purified by preparative TLC (2 mm silica gel, 6.5: 3.5 ethyl acetate/hexane) to yield 320 mg (33.8% from hydrobenzamide) of the title compound 25 as a 2.7:1 mixture of diastereomers [(3R, 4S)/(3S, 4R)]and as an oil. ¹H NMR [(3R, 4S)-diastereomer, CDCl₃, 200 MHz]: δ=7.27–7.44 (m, 5H, Ph), 6.54 (br s, exchangeable, 1H, NH), 5.07 (dd, J-2.7, 4.5 Hz, 1H, H-3), 5.00 (br s, 1H), 4.89 (d, J=4.5 Hz, 1H, H-4), 4.49 (H, J=4.0, 10.5 Hz, 1H), 4.01–4.14 (m, 1H), 3.93 (dd, J=4.5, 12.5 Hz, 1H), 3.70 (dd, J=1.5, 12.5 Hz, 1H), 2.49–2.59 (m, 1H), 2.06 (s, 3H, OAc) 1.94 (s, 3H, OAc), 1.57–1.93 (m, 3H). ¹H NMR [(3S, 4R)-diastereomer, CDCl₃, 200 MHz]: δ=7.28–7.39 (m, 5H, Ph), 6.30 (br s, exchangeable, 1H, NH), 5.17 (dd, J=2.7, 4.4 Hz, 1H, H-3), 4.88 (d, J=4.4 Hz, 1H, H-4), 4.64 (H, J=5.3, 10.1 Hz, 1H), 4.13–4.35 (m, 2H), 4.04–4.12 (m, 2H), 2.04 (s, 3H, OAc), 2.01 (s, 3H, OAc), 1.61–1.86 (m, 2H), 1.34–1.54 (m, 1H), 1.04–1.19 (m, 1H).

Reasonable variations, such as those which would occur to a skilled artisan, can be made herein without departing from the scope of the invention.

We claim:

1. A cis compound having the formula:

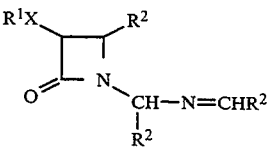

wherein $R^1$ is selected from the group consisting of: alkyl, halo-substituted alkyl, aryl, cycloalkyl, and arylalkyl; X is selected from O, N, S, C(O)O and a direct bond; and $R^2$ is selected from the group consisting of aryl, aryl bearing from 1 to 3 of the same or different substituents selected from $C_{1-3}$ alkyl, $C_{1-3}$ alkoxy, hydroxy, trifluoromethyl and halogen, and heteroaryl.

2. A compound of claim 1 wherein $R^2$ is selected from the group consisting of phenyl, 4-methylphenyl, and 4-methoxyphenyl.

3. A compound of claim wherein $R^1$ is selected from the group consisting of alkyl, chloroalkyl and phenyl.

4. A compound of claim 2 wherein $R^1$ is methyl.

5. A compound of claim 2 wherein $R^2$ is phenyl.

6. A compound of claim 5 wherein $R^1$ is chloromethyl or phenyl.

7. A compound of claim 1 wherein $R^2$ is selected from the group consisting of furyl and thienyl.

8. A compound of claim 7 wherein $R^1$ is selected from the group consisting of alkyl, chloroalkyl and phenyl.

* * * * *